(12) United States Patent
Thompson (10) Patent No.: US 8,535,259 B2
(45) Date of Patent: Sep. 17, 2013

(54) METHODS FOR BILIARY DIVERSION (75) Inventor: Suzanne Thompson, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 198 days.

(21) Appl. No.: 12/980,680

(22) Filed: Dec. 29, 2010

(65) Prior Publication Data

US 2012/0172782 A1 Jul. 5, 2012

(51) Int. Cl.
*A61M 5/00* (2006.01)
*A61M 31/00* (2006.01)

(52) U.S. Cl.
USPC .................................. 604/8; 604/9; 604/500

(58) Field of Classification Search
USPC .................................. 604/8, 9, 500
See application file for complete search history.

(56) References Cited

U.S. PATENT DOCUMENTS

| | | | |
|---|---|---|---|
| 5,792,095 A * | 8/1998 | Kissinger et al. | 604/9 |
| 7,314,489 B2 | 1/2008 | McKenna et al. | |
| 7,618,427 B2 | 11/2009 | Ortiz et al. | |
| 2003/0032967 A1 | 2/2003 | Park et al. | |
| 2003/0069533 A1 | 4/2003 | Kakutani et al. | |
| 2005/0085787 A1 | 4/2005 | Laufer | |
| 2005/0096750 A1 | 5/2005 | Kagan et al. | |
| 2006/0106332 A1 | 5/2006 | Knudson et al. | |
| 2008/0208161 A1 | 8/2008 | Kaji et al. | |
| 2008/0243151 A1* | 10/2008 | Binmoeller et al. | 606/153 |
| 2009/0062717 A1 | 3/2009 | Laufer | |
| 2009/0264808 A1* | 10/2009 | Young | 604/8 |
| 2010/0069819 A1 | 3/2010 | Laufer | |
| 2010/0076462 A1 | 3/2010 | Bakos et al. | |
| 2010/0076488 A1 | 3/2010 | Spivey et al. | |
| 2010/0106166 A1 | 4/2010 | Cropper et al. | |
| 2010/0191167 A1 | 7/2010 | Laufer | |

FOREIGN PATENT DOCUMENTS

| | | | |
|---|---|---|---|
| GB | 2460287 A | * | 11/2009 |
| WO | WO-2004087233 A2 | | 10/2004 |
| WO | WO-2005037073 A2 | | 4/2005 |
| WO | WO-2007050628 A2 | | 5/2007 |
| WO | WO-2007103773 A2 | | 9/2007 |

OTHER PUBLICATIONS

"Placement of PD Catheters." Advanced Renal Education Program. Fresnius Medical Care North America, Jun. 12, 2008. Web. Aug. 29, 2012. <http://www.advancedrenaleducation.com/Peritoneal Dialysis/DialysisAccess/PlacementofPDCatheters/tabid/162/Default.asp &xgt;.*

"SpyGlass" Direct Visualization System from Boston Scientific Website, dated Aug. 2008 (2 pages).

(Continued)

*Primary Examiner* — Tatyana Zalukaeva
*Assistant Examiner* — Andrew J Mensh
(74) *Attorney, Agent, or Firm* — Nutter McClennen & Fish LLP (57) ABSTRACT

Methods are provided for biliary diversion. In one embodiment, a tubular member can be implanted within a patient by positioning a proximal end of the tubular member in the patient's gall bladder, positioning a distal end of the tubular member in the patient's intestine, and positioning a length of the tubular member extending between the proximal and ends thereof within the patient's stomach. Bile can therefore be allowed to pass from the gall bladder into the tubular member's proximal end, flow through the tubular member, and exit through the tubular member's distal end to enter the patient's gastrointestinal tract at the intestine.

17 Claims, 6 Drawing Sheets

(56) References Cited

OTHER PUBLICATIONS

Ernest J. Ring, "Percutaneous Intubation Of Malignant Biliary Strictures," Chapter 15 in "Advances in and Surgical Treatment of Biliary Tract Disease," ed. Moody et al., 1983.

Rudnicki et al., "A Simple Method For Biliary-Enteric Anastomosis And Chronic Bile Diversion In The Rat," Hepatology, Jul. 1991, 14(1): 128-130.

App. No. PCT/EP2010/060275 filed Jul. 16, 2010.

* cited by examiner

METHODS FOR BILIARY DIVERSION

FIELD OF THE INVENTION

The present invention relates to methods for biliary diversion.

BACKGROUND OF THE INVENTION

Numerous non-operative therapies for morbid obesity have been tried in the past with virtually no permanent success. Surgical methods of treating morbid obesity, such as open, laparoscopic and endoluminal gastric bypass surgery aiming to permanent malabsorption of the food, have been increasingly used with greater success. However, current methods for performing a gastric bypass involve time-consuming and highly dexterity dependent surgical techniques as well as significant and generally highly invasive modifications of the patient's gastrointestinal anatomy. These procedures are reserved only for the severely obese patients because they have a number of significant complications, including the risk of death.

Accordingly, there is a need for methods which avoid the drawbacks of gastric bypass surgery and influence the digestion of a patient in a more specific and aimed way, such as primarily influencing and modifying entero-hepatic bile cycling rather than the digestive tract itself.

SUMMARY OF THE INVENTION

The present invention generally provides methods for biliary diversion. In one embodiment, a surgical method if provided that includes positioning a first terminal end of a tubular member in a gall bladder of a patient, positioning an intermediate portion of the tubular member through a stomach of the patient, and positioning a second terminal end of the tubular member in an intestine of the patient to allow bile in the gall bladder to flow into an inner lumen of the tubular member through the first terminal end of the tubular member, flow through the inner lumen in the intermediate of the tubular member through the stomach, and flow out of the inner lumen at the second terminal end of the tubular member and into the intestine. Positioning the first terminal end of the tubular member, positioning the intermediate portion of the tubular member, and positioning the second terminal end of the tubular member can be performed using an instrument inserted through a natural orifice of the patient.

The first and second ends of the tubular member can be positioned in any number of ways. Positioning the first terminal end of the tubular member can include attaching the tubular member to a wall of the gall bladder with at least one anchor. Positioning the second terminal end of the tubular member can include applying a weight to the tubular member configured to maintain the second terminal end of the tubular member in the intestine. The second terminal end of the tubular member can be positioned at any location in the intestine, such as at a jejunum of the intestine.

The method can have any number of variations. For example, a common bile duct of the patient can be obstructed such that bile in the gall bladder cannot flow through the common bile duct to the intestine, and such that pancreatic fluid can flow from a pancreas of the patient to the intestine. For another example, a seal can be formed between the gall bladder and the stomach such that bile from the gall bladder cannot flow into the stomach to contact an inner wall of the stomach. For still another example, a wall of the gall bladder can be secured to a wall of the stomach, e.g., by applying at least one anchor to the wall of the gall bladder and to the wall of the stomach. The at least one anchor can be bioabsorbable. The wall of the gall bladder and the wall of the stomach can be incised proximate to the securement of the wall of the gall bladder to the wall of the stomach, and the tubular member can pass from the gall bladder to the stomach through the incisions formed in the wall of the gall bladder to the wall of the stomach.

In another embodiment, a surgical method is provided that includes advancing an endoscope into a stomach of a patient to visualize a gall bladder of the patient through a wall of the stomach, attaching a wall of the gall bladder to the wall of the stomach, positioning a proximal end of a tubular member in the gall bladder, positioning an intermediate portion of the tubular member through the stomach, and positioning the distal end of the tubular member in an intestine of the patient such that bile can flow in the tubular member from the gall bladder, through the intermediate portion of the tubular member, and to the intestine. The tubular member can form a barrier between bile flowing therethrough and the stomach such that bile cannot come into direct contact with an inner wall of the stomach.

The method can vary in any number of ways. For example, the endoscope can be advanced through a mouth and an esophagus of the patient. For another example, the endoscope can be removed from the patient, and the tubular member can be left implanted in the patient with the proximal end of the tubular member positioned in the gall bladder, the intermediate portion of the tubular member positioned in the stomach, and the distal end of the tubular member positioned in the intestine. For still another example, a common bile duct of the patient can be obstructed such that bile in the gall bladder cannot flow through the common bile duct to the intestine, and such that pancreatic fluid can flow from a pancreas of the patient to the intestine.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods are provided for biliary diversion, e.g., diversion of biliary secretions. In general, the methods allow bile to be diverted from the gall bladder to the intestine. In an exemplary embodiment, a tubular member can be implanted within a patient by positioning a proximal end of the tubular member in the patient's gall bladder, positioning a distal end of the tubular member in the patient's intestine, and positioning a length of the tubular member extending between the proximal and ends thereof within the patient's stomach. Bile can therefore be allowed to pass from the gall bladder into the tubular member's proximal end, flow through the tubular member, and exit through the tubular member's distal end to enter the patient's gastrointestinal tract at the intestine. The tubular member can be unidirectional such that materials within the intestine, e.g., partially digested food and acidic chime, can be prevented from flowing from the intestine and into the gall bladder, which can reduce risks of lumen clogging and infection due to backflow, e.g., chime-related infections of the biliary tree and pancreatitis. The distal end of the tubular member can be positioned at any location in the intestine, but in an exemplary embodiment, the tubular member's distal end can be positioned distal to the patient's ampulla of Vater, e.g., downstream of the ampulla of Vater. In this way, bile can flow directly from the gall bladder to a location distal of its natural entrance into the intestine at the ampulla of Vater. The bile can thus encounter and mix with food in the intestine at a time later in the digestive cycle than it would naturally, e.g., with bile flowing through the patient's common bile duct and entering the intestine through the ampulla of Vater where it naturally encounters and mixes with food. This later encountering and mixing of bile with food can alter the patient's metabolism and result in changes in energy expenditure, appetite, and/or regulation of glucose and/or insulin. By connecting the gall bladder and the intestine with a tubular member fed through the stomach, the intestine need not be anatomically displaced, punctured, or incised to redirect bile thereto, which can help reduce surgical handling of the delicate intestine and help avoid complications which can arise from displacing, puncturing, or incising the intestine, e.g., infection, patient discomfort, etc. Also by connecting the gall bladder and the intestine with a tubular member fed through the stomach, a tubular member need not be positioned in the common biliary duct or extend through the ampulla of Vater, thereby reducing if not eliminating a risk of pancreatis.

While the devices and methods disclosed herein can be used in conventional, open surgical procedures, they are particularly useful in minimally invasive surgical procedures, such as endoscopic procedures. A person skilled in the art will also appreciate that the present invention has application in conventional open surgical and minimally invasive instrumentation as well application in robotic-assisted surgery. The principles described herein can be applicable to the particular types of tools described herein and to a variety of other surgical tools having similar functions. In addition, the tools can be used alone in a surgical procedure, or they can be used in conjunction with other devices that facilitate minimally invasive surgical procedures.

Figure 1:
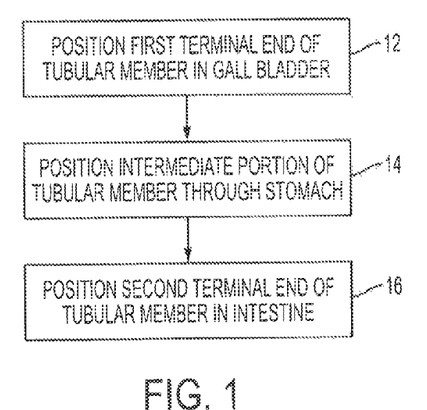
FIG. 1 is a flowchart showing one embodiment of a biliary diversion surgical procedure.

In one exemplary embodiment, illustrated in FIG. 1, a biliary diversion surgical procedure 10 can be performed on a patient. Generally, the procedure 10 can include positioning 12 a first terminal end of a tubular member in a gall bladder of the patient. The tubular member can include any cannulated, biocompatible device configured to be implanted within a body, e.g., a catheter, a stent, etc. Although the tubular member can be formed from any one or more flexible materials, in an exemplary embodiment, the tubular member can be formed from silicone or polyurethane. The tubular member can have a variety of sizes, shapes, and configurations. In an exemplary embodiment, the tubular member can have a size in a range of about 10 to 15 Fr. The tubular member can have any longitudinal length extending between terminal ends thereof, e.g., a length sufficient to extend between a patient's gall bladder and the patient's intestine. As discussed further below, the tubular member can be expandable or collapsible, such as with an expandable bellows having an adjustable longitudinal length. An expandable or collapsible tubular member can have a size greater than about 15 Fr. The tubular member can be flexible, e.g., be configured to curve or bend while allowing fluid to pass through its cannulated interior. In this way, the tubular member can be implanted within a patient and curve or bend within the patient as necessary to navigate the patient's anatomy between the patient's gall bladder and intestine while allowing fluid to flow through the tubular member's cannulated interior from the gall bladder to the intestine. The tubular member can include one inner lumen extending therethrough, but as will be appreciated by a person skilled in the art, the tubular member can instead include a plurality of inner lumens. Having a plurality of inner lumens can provide redundancy if a lumen clogs.

The tubular member can optionally include a unidirectional valve configured to allow a fluid to flow in a first direction and to prevent the fluid from flowing in a second, opposite direction. In other words, the unidirectional valve can be configured to prevent backflow, such as by allowing fluid, e.g., bile, to pass into the tubular member from the gall bladder through the first terminal end while preventing fluid, e.g., bile, acidic chime, etc., located within the tubular member from flowing out of the tubular member through the first terminal end and into the gall bladder. The unidirectional valve can thus be configured to help prevent infection or pancreatitis caused by partially digested food or other unwanted matter entering the gall bladder through the first terminal end of the tubular member. As will be appreciated by a person skilled in the art, the unidirectional valve can include any mechanism configured to allow fluid flow therethrough in only one direction, such as a check valve, e.g., a ball check valve, a duckbill, a stop-check valve, etc.

The procedure 10 can also include positioning 14 an intermediate portion of the tubular member through a stomach of the patient and positioning 16 a second terminal end of the tubular member in an intestine of the patient. In this way, the tubular member can extend between the gall bladder and the intestine, with a portion of the tubular member extending between the first and second terminal ends being located within a cavity of the stomach to allow bile to flow from within the gall bladder to within the intestine. Although the procedure 10 is illustrated in FIG. 1 with the tubular member's first terminal end first being positioned 12 in the gall bladder, the tubular member's intermediate portion next being positioned 14 through the stomach, and then the tubular member's second terminal end being positioned 16 in the intestine, the procedure 10 can be performed in any order, e.g., positioning 16 the tubular member's second terminal end in the intestine followed by positioning 14 the tubular member's intermediate portion through the stomach and positioning 12 the tubular member's first terminal end in the gall bladder.

Any length of the tubular member can be positioned 14 through the stomach. In an exemplary embodiment, the intermediate portion of the tubular member can include a midpoint of the tubular member such that the midpoint of the tubular member can be located within the stomach when the tubular member is positioned 14 therethrough.

The tubular member's second terminal end can be positioned 16 at any location in the intestine, but in an exemplary embodiment, the tubular member's second terminal end can be positioned 16 in the small intestine distal to the patient's ampulla of Vater, e.g., downstream of the ampulla of Vater, such that a portion of the tubular member can be positioned in a duodenum of the intestine. In an exemplary embodiment, the tubular member's distal end can be positioned 16 distal to, e.g., downstream of, the duodenum, e.g., in a jejunum of the intestine or in an ileum of the intestine. For non-limiting example, the tubular member's second terminal end can be positioned 16 in a region between a proximal-most end of the jejunum and a midpoint of the jejunum. As mentioned above, if the tubular member includes a unidirectional valve, the unidirectional valve can be positioned within the tubular member between the first and second terminal ends thereof, and thereby be configured to prevent any acidic chime or other matter that has entered the tubular member from the intestine through the second terminal end from flowing out of the tubular member through the first terminal end and into the gall bladder.

Figure 2:
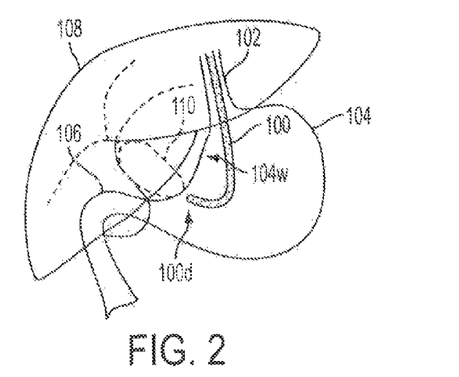
FIG. 2 is a perspective, partially transparent view showing one embodiment of an endoscope advanced into a stomach of a patient.

A biliary diversion surgical procedure, such as the procedure 10 of FIG. 1, can be performed in a variety of ways using a variety of surgical tools. In one exemplary embodiment of a biliary diversion surgical procedure, as illustrated in FIG. 2, an esophagus 102, a stomach 104, and a proximal portion of a duodenum 106 of the patient can be visualized using a scoping device, e.g., an endoscope 100, advanced into a patient. In this way, the endoscope 100 can be used to screen the patient and perform an esophagogastroduodenoscopy (EGD). An ultrasonic endoscopic probe is illustrated in FIG. 2 as the endoscope 100, but as will be appreciated by a person skilled in the art, any scoping device can be used, and the stomach 104 can be visualized in any way. As illustrated in FIG. 2, at least a distal end 100d of the endoscope 100 can be advanced through the patient's mouth (not shown), through the esophagus 102, and into the stomach 104. However, as will also be appreciated by a person skilled in the art, the endoscope 100 can be advanced into the patient in any way through a natural orifice of the patient or through an artificially created opening or incision formed in the patient. As will be appreciated by a person skilled in the art, the stomach 104 can be insufflated before, during, and/or after advancement of the endoscope 100 into the patient.

The procedure can also include identifying and locating a gall bladder 110 of the patient that is positioned adjacent a liver 108 of the patient. As in the illustrated embodiment of FIG. 2, the endoscope 100 positioned in the stomach 104 can ultrasonically image the gall bladder 110 through a wall, such as an intestinal wall or a wall 104w of the stomach 104, e.g., through an anterior surface of the stomach 104 near the stomach's lesser curvature, to allow identification and location of the gall bladder 110. However, as will be appreciated by a person skilled in the art, the gall bladder 110 can be identified and located in any way using any one or more tools, such as by using a non-ultrasonic scoping device configured to image the gall bladder 110 through a tissue wall such as the stomach wall or the intestinal wall.

Having properly identified and located the gall bladder 110, the gall bladder 110 can be secured to the stomach 104, e.g., a "-pexy" can be formed. Such securing can be performed in a variety of ways, as will be appreciated by a person skilled in the art. In one exemplary embodiment, the gall bladder 110 can be secured to the stomach 104 by applying at least one anchor to a wall 110w of the gall bladder 110 and to the wall 104w of the stomach 104. The at least one anchor can be applied to the stomach and bladder walls 104w, 110w in any way, as will be appreciated by a person skilled in the art. As will also be appreciated by a person skilled in the art, the at least one anchor can include any type of attachment mechanism, such as a clip, a staple, a tied suture, an adhesive etc. If multiple anchors are used, each of the anchors can be the same as or different from any of the other anchors.

Figure 3:
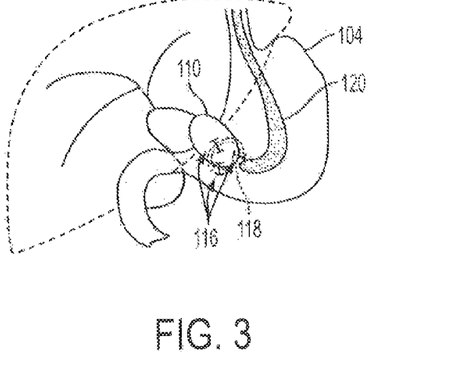
FIG. 3 is a perspective, partially transparent view showing one embodiment of a gastroscope advanced into the stomach of FIG. 2 to visualize a plurality of anchors applied to the stomach and to a gall bladder of the patient.

In one exemplary embodiment, as illustrated in FIG. 3, the at least one anchor used to secure the stomach 104 and the gall bladder 110 together can include a plurality of suture anchors 116. Although three anchors 116 are illustrated in FIG. 3, any number of anchors, same or different from one another, can be used to secure the gall bladder 110 and the stomach 104 to one another. The anchors 116 can optionally be bioabsorbable such that a subsequent surgical procedure need not be performed on the patient to remove the anchors 116 therefrom. The plurality of anchors 116 can be applied to the stomach 104 and the bladder 110 in any arrangement. In an exemplary embodiment, as shown in FIG. 3, the anchors 116 can be spaced apart from one another, e.g., substantially equidistantly spaced from one another, such that an area 118 of substantial contact between outer surfaces of the stomach and bladder walls 104w, 110w can be formed. The area 118 can be configured to facilitate advancement of a surgical device from within the stomach 104, through the stomach and bladder walls 104w, 110w, and into the bladder 110, as discussed further below. The area 118 can have any shape and size, e.g., about 2 cm². As will be appreciated by a person skilled in the art, the suture anchors 116 can be applied to tissue using any one or more surgical instrument, e.g., a surgical instrument advanced through a working channel of the endoscope 100. Various non-limiting embodiments of suture anchors and devices configured to apply suture anchors to tissue can be found in U.S. Pat. Pub. No. 2010/0106166 filed Oct. 29, 2008 and entitled "Methods And Devices For Applying Multiple Suture Anchors," U.S. Pat. Pub. No. 2010/0076462 filed Sep. 25, 2008 and entitled "Methods And Devices For Delivering And Applying Suture Anchors," and U.S. Pat. Pub. No. 2010/0076488 filed Sep. 25, 2008 and entitled "Methods And Devices For Delivering And Applying Multiple Suture Anchors," which are hereby incorporated by reference in their entireties.

Figure 4:
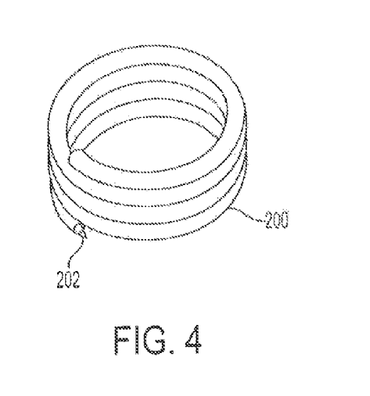
FIG. 4 is a perspective view of one embodiment of a tissue clamping coil.
Figure 5:
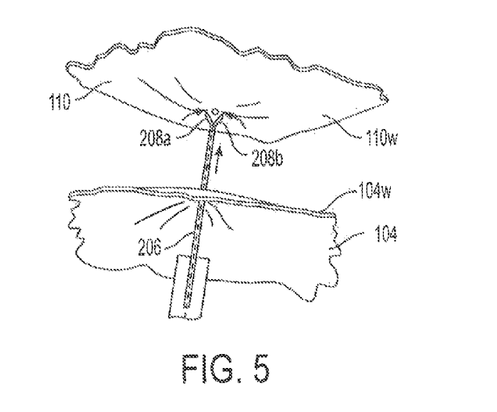
FIG. 5 is a perspective view of one embodiment of an anastomosis instrument delivering the tissue clamping coil of FIG. 4 to stomach and gall bladder walls.
Figure 6:
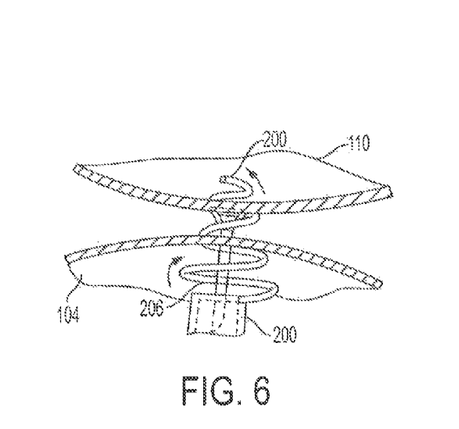
FIG. 6 is a perspective view of the anastomosis instrument of FIG. 5 deploying the tissue clamping coil.
Figure 7:
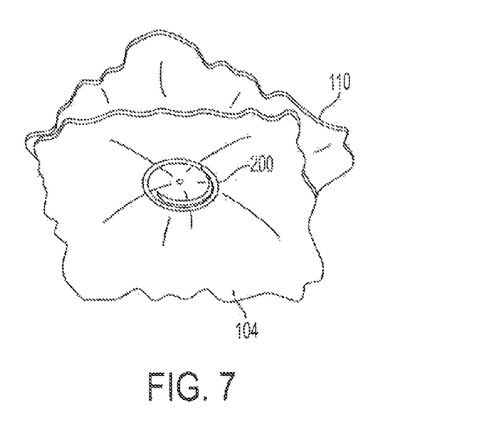
FIG. 7 is a perspective view of the tissue clamping coil of FIG. 6 applied to the stomach and gall bladder walls.

In another exemplary embodiment, the at least one anchor used to secure the stomach 104 and the gall bladder 110 together can include at least one tissue clamping coil. Various non-limiting embodiments of tissue clamping coils can be found in PCT App. No. PCT/EP2010/060275 filed Jul. 16, 2010 and entitled "A Device And Method For Directing Bile From The Gallbladder In the Intestine" and in U.S. Pat. No. 7,618,427 filed Sep. 22, 2004 entitled "Device And Method For Intralumenal Anastomosis," which are hereby incorporated by reference in their entireties. One exemplary embodiment of a tissue clamping coil 200 is illustrated in FIG. 4. The coil 200 can have a pointed tip 202 and can be formed from a shape memory alloy, e.g., a TiNi alloy, wire annealed in a coil shape and subsequently longitudinally straightened in a stressed shape. The coil 200 can be applied to the stomach and bladder walls 104w, 110w to attach the stomach 104 and gall bladder 110 together using, e.g., an anastomosis instrument 204, as illustrated in one embodiment in FIGS. 5-7. Generally, a surgical tool, e.g., a grasper 206 having two opposed jaws 208a, 208b, can be advanced through the stomach wall 104w such that at least a distal end of the grasper 206 moves from one side of the stomach wall 104w to another, opposite side of the stomach wall 104w, e.g., moves from a location inside the stomach 104 to a location outside the stomach 104. As illustrated in FIG. 5, the grasper 206 can be advanced through an opening or incision formed in the stomach wall 104w prior to advancing the grasper 206 therethrough, or the grasper 206 can be configured to form the opening or incision as the grasper 206 is advanced through the stomach wall 104w. The jaws 208a, 208b can be used to grasp the wall 110w of the gall bladder 110 and pull the bladder wall 110w toward the stomach 104 such that the stomach and bladder walls 104w, 110w are near one another, if not in direct contact with one another. With the gall bladder 110 and the stomach 104 at an appropriate distance from one another, the anastomosis instrument 204 can be used to apply coil 200 to the gall bladder 110 and the stomach 104 to secure the two together, as illustrated in FIGS. 6 and 7.

Figure 8:
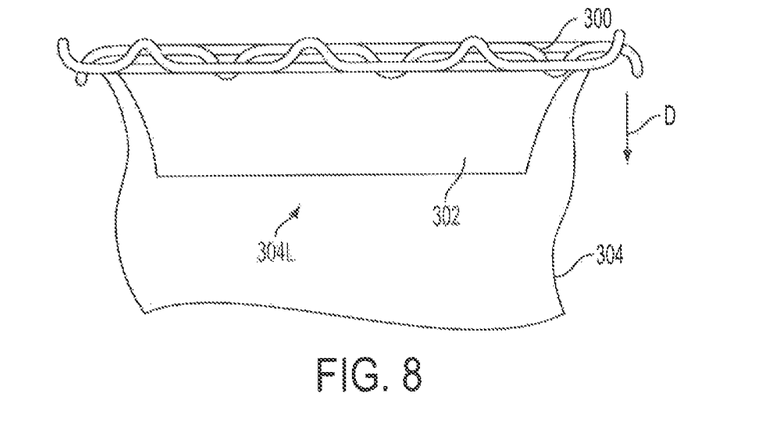
FIG. 8 is a perspective view of one embodiment of a woven tube including a duckbill valve shutter, the duckbill valve shutter being in an open configuration.
Figure 9:
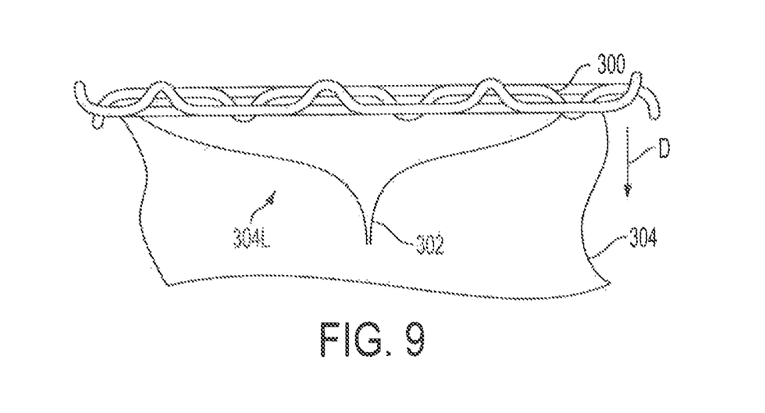
FIG. 9 is a perspective view of the woven tube of FIG. 8, the duckbill valve shutter being in a closed configuration.

In another exemplary embodiment, the at least one anchor used to secure the stomach 104 and the gall bladder 110 together can include at least one woven tube of wire. Various non-limiting embodiments of woven tubes and elongate applicators configured to deploy woven tubes can be found in previously mentioned PCT App. No. PCT/EP2010/060275 filed Jul. 16, 2010 and entitled "A Device And Method For Directing Bile From The Gallbladder In the Intestine" and in U.S. Pat. Pub. No. 2003/0032967 filed Jun. 20, 2002 and entitled "Anastomotic Device," which is hereby incorporated by reference in its entirety. One exemplary embodiment of a woven tube 300 of wire is illustrated in FIGS. 8 and 9. The woven tube 300 can be formed from a shape memory alloy wire and have outer loops or ends configured to thermally deform and evert when inserted into adjacent tissue walls, e.g., the stomach and bladder walls 104w, 110w. By thermally deforming and everting, the ends of the woven tube 300 can form petals in a manner which clamps the adjacent tissue walls in apposition. The woven tube 300 can be applied to tissue in any way, such as by deploying the woven tube 300 from a surgical instrument such as an elongate applicator (not shown) advanced through a working channel of the endoscope 100.

The woven tube 300 can optionally include a unidirectional valve, such as a duckbill valve shutter 302 as illustrated in FIGS. 8 and 9. The duckbill valve shutter 302 can be formed from a synthetic elastomer and have a shape like the beak of a duck with a flattened end which elastically retains its flattened shape. The duckbill valve shutter 302 can be configured to allow fluid to flow therethrough in a direction D. The woven tube 300 including the duckbill valve shutter 302 can be secured to the stomach and bladder walls 104w, 110w in an orientation that allows fluid to flow through the duckbill valve shutter 302 in the direction D from the gall bladder 110 toward the stomach 104. In this way, when the woven tube 300 including the duckbill valve shutter 302 is secured to the stomach and bladder walls 104w, 110w, when bile pressure in the gall bladder 110 reaches a certain threshold value, the duckbill valve shutter 302 can move from a closed configuration, illustrated in FIG. 9, in which bile from the gall bladder 110 cannot flow therethrough in the direction D, to an open configuration, illustrated in FIG. 8, in which bile can flow therethrough in the direction D. In other words, the flattened end of the duckbill valve shutter 302 can open to permit the bile to pass through the duckbill valve shutter 302 into an inner lumen 304L of a flexible tubular member 304 attached to the woven tube 300 and having the duckbill valve shutter 302 positioned therein. Bile from the gall bladder 110 can thus enter the tubular member 304 through a first terminal end thereof in the gall bladder 110 and flow therethrough to an intestine of the patient, as discussed further below, with the duckbill valve shutter 302 preventing bile or other material in the inner lumen 304L from passing into the gall bladder 110. Although the duckbill valve shutter 302 is positioned adjacent a terminal end of the tubular member 304 in the illustrated embodiment, the duckbill valve shutter 302 can be positioned anywhere within the tubular member's inner lumen 304L, e.g., in an intermediate portion thereof, such as at a mid-point thereof As will be appreciated by a person skilled in the art, the duckbill valve shutter 302 and the tubular member 304 can be formed on or connectable to the woven tube 300 in any way, and the duckbill valve shutter 302 can be incorporated in or attached to the tubular member 304 in any way.

With the gall bladder 110 secured to the stomach 104, the ultrasonic endoscopic probe 100 can be removed from the patient, and the patient can be reintubated with a non-ultrasonic scoping device to visualize, e.g., the stomach 104 and the gall bladder 110. A person skilled in the art will appreciate that, in some embodiments, reintubation is unnecessary, e.g., if a single scoping device is advanced into a patient and remains positioned therein throughout its desired use during a surgical procedure. Referring again to the embodiment illustrated in FIG. 3, with the anchors 116 securing the gall bladder 110 to the stomach 104, a gastroscope 120 can be advanced through the patient's mouth, through the esophagus 102, and into the stomach 104 to provide visualization of, e.g., the stomach 104 and the gall bladder 110. A gastroscope, e.g., a flexible surgical instrument configured to be advanced into a patient and to provide visualization therein, is shown as the non-ultrasonic scoping device in the illustrated embodiment of FIG. 3, but as well be appreciated by a person skilled in the art, any scoping device can be used for reintubation, and any device can be used for visualization, e.g., indirect imaging, of the gall bladder 110.

With the gall bladder 110 secured to the stomach 104, an opening, puncture, or incision, generally referred to as an "incision," can be formed through the stomach and bladder walls 104w, 110w, e.g., an incision can be formed through each of the stomach and bladder walls 104w, 110w to effectively form a single incision through the stomach and bladder walls 104w, 110w. Although incisions can be formed each of the stomach and bladder walls 104w, 110w before the gall bladder 110 and the stomach 104 are secured together, e.g., before at least one anchor is applied thereto, forming incisions through the stomach and bladder walls 104w, 110w with the gall bladder 110 secured to the stomach 104 can help ensure that the incisions formed through the walls 104w, 110w are substantially aligned to facilitate advancement of a surgical instrument therethrough.

Figure 10:
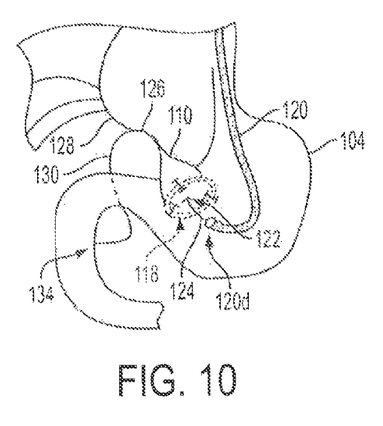
FIG. 10 is a perspective, partially transparent view showing one embodiment of a cutting instrument advanced into the stomach through the gastroscope of FIG. 3 and forming an incision in the stomach and the gall bladder.

In an exemplary embodiment, as illustrated in FIG. 10, an incision 122 can be formed in the area 118 of substantial contact between the gall bladder 110 and the stomach 104. The incision 122 can facilitate application of at least one obstructor and/or at least one tubular member within the patient, as discussed further below. Forming the incision in the area 118 can help create incisions formed through the walls 104w, 110w that are substantially aligned with one another, which can help facilitate advancement of a surgical instrument through the incision 122. The incision 122 can be formed in the stomach and bladder 104w, 110w walls in any way, as will be appreciated by a person skilled in the art. In an exemplary embodiment, the incision 122 can be formed with a distal end of the gastroscope 120 positioned in the stomach 104 and providing visualization of the area 118 of substantial contact between the gall bladder 110 and the stomach 104 to facilitate formation of the incision within the area 118. As in the illustrated embodiment, a cutting instrument 124, e.g., a needle knife, a scalpel, scissors, a hook knife, a blunt dissector, a cautery tool configured to cut tissue, an endoscopic linear cutter, etc., can be advanced through a working channel of the gastroscope 120. A distal end of the cutting instrument 124 can be advanced distally beyond a distal end 120d of the gastroscope 120 to facilitate formation of the incision 122 using, e.g., a sharp distal tip, of the cutting instrument 124. The surgical tool used to secure the stomach 104 and the bladder 110 together, e.g., used to apply the anchors 116 thereto, can, in some embodiments, also be configured to and used to form the incision 122.

Optionally, a surgical instrument (not shown) configured to provide visualization can be advanced through the incision 122 in a direction from the stomach 104 to the bladder 110 to visualize one or more areas of the patient's anatomy in preparation of application of at least one obstructor and/or at least one tubular member within the patient, as discussed further below. For non-limiting example, the surgical instrument can visualize the gall bladder 110, a cystic duct 126 of the patient, a common hepatic duct 128 of the patient, a common bile duct 130 of the patient, and/or the stomach 104. In an exemplary embodiment, a relatively small scoping device, e.g., a SpyGlass® Fiber Optic Probe available from Boston Scientific Corporation of Natick, Mass., can be advanced through a working channel of the gastroscope 120 and advanced distally beyond the distal end 120d thereof to be advanced from within the stomach 104, through the incision 122, and into the gall bladder 110.

In one exemplary embodiment, total biliary diversion can be accomplished by applying at least one obstructor, occlude, or plug, generally referred to as a "plug," to the biliary tract of the patient, and by positioning at least one tubular member between the gall bladder 104 and the intestine 106. However, in another exemplary embodiment, the plug need not be applied such that partial biliary diversion can be accomplished. The plug can have a variety of sizes, shapes, and configurations, and can be applied in a variety of ways. The plug can be bioabsorbable and/or can be configured to be removable, e.g., removed from the patient in a subsequent surgical procedure. One exemplary embodiment of a plug includes a vascular type occlusion device.

Figure 11:
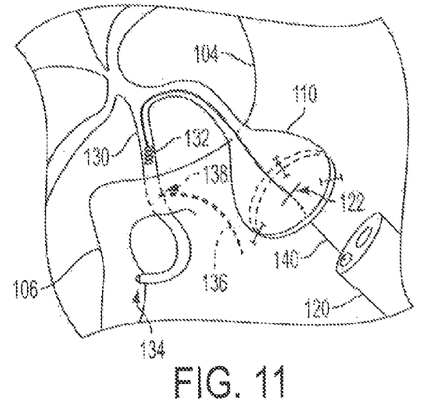
FIG. 11 is a perspective, partially transparent view showing one embodiment of an applicator device advanced into the stomach through the gastroscope of FIG. 10 and applying a plug to a common bile duct.

One exemplary embodiment of total biliary diversion including application of a plug 132 to the common bile duct 130 is illustrated in FIG. 11. As mentioned above, the plug 132 can be applied in any way, as in the illustrated embodiment, the plug 132 can be applied using an applicator device 140 advanced into the patient's stomach 104 through a working channel 120c of the gastroscope 120, through the incision 122, and through the gall bladder 104 to position the plug 132 within the common bile duct 130. Although the plug 132 is positioned within the common bile duct 130 in the illustrated embodiment, the plug 132 can be positioned at any location within the patient's biliary tract to achieve total biliary diversion, e.g., to prevent bile in the gall bladder 110 from passing into the intestine 106 through an ampulla of Vater 134 of the patient. Instead of passing through the ampulla of Vater 134, the bile can be diverted to the intestine 106 along another path, such as through a tubular member, as discussed further below. In an exemplary embodiment, the plug 132 can be positioned in the common bile duct 130 such that bile in the gall bladder 110 cannot flow through the common bile duct 130 to enter the intestine 106 through the ampulla of Vater 134, while still allowing a natural flow of pancreatic fluid through a pancreatic duct 136 of the patient from a pancreas (not shown) of the patient to the intestine 106. For non-limiting example, the plug 132 can be positioned within the common bile duct 130 proximal to, e.g., upstream of, an intersection point 138 where the pancreatic duct 136 meets the common bile duct 130. In this way, total biliary diversion can be achieved while allowing normal drainage of the pancreas. In some embodiments, the plug 132 can be positioned within the common bile duct 130 distal to the pancreatic duct 136 to achieve total biliary diversion and total pancreatic diversion.

With the plug 132 applied to the patient's biliary tract, bile cannot flow into the intestine 106 as would naturally occur. To prevent build-up of bile in the gall bladder 110 and to allow bile to perform its typical function in the intestine 106, bile can be diverted from the gall bladder 110 to the intestine 106 via a tubular member extending between the gall bladder 110 and the intestine 106. However, as mentioned above, in some embodiments, partial biliary diversion can be achieved with the tubular member being applied to extend between the gall bladder 110 and the intestine 106 to allow bile to flow therethrough while also allowing bile to naturally flow through the common bile duct 130 to enter the intestine 106 through the ampulla of Vater 134. Generally, as also mentioned above, the tubular member can have a variety of sizes, shapes, and configurations and can be applied to a patient in any way. Generally, the tubular member can be implanted in the patient such that a proximal end of the tubular member is positioned in the gall bladder 110, an intermediate portion of the tubular member is positioned through the stomach 104, and a distal end of the tubular member is positioned in the intestine 106. In this way, bile can flow through the tubular member to reach the intestine 106 even when the plug 132 blocks the bile's natural pathway to the intestine 106.

Figure 12:
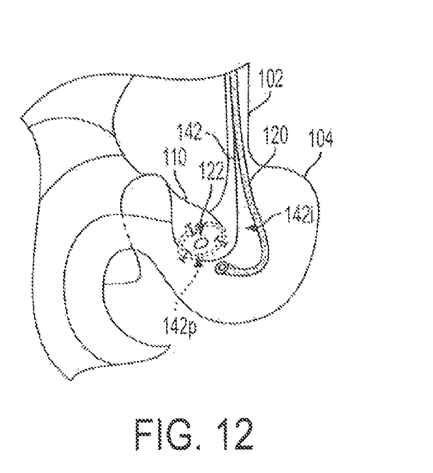
FIG. 12 is a perspective, partially transparent view showing one embodiment of a proximal end of a tubular member being positioned in the gall bladder adjacent the incision of FIG. 10.
Figure 13:
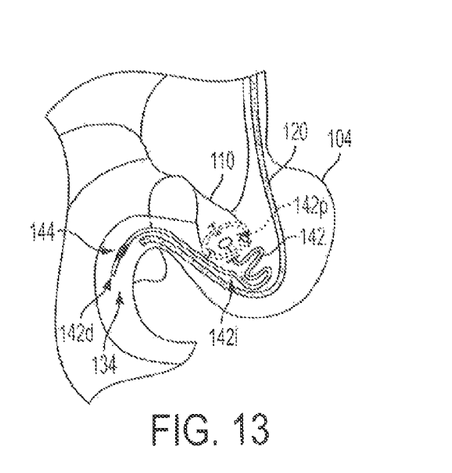
FIG. 13 is a perspective, partially transparent view showing an intermediate portion of the tubular member of FIG. 12 being positioned in the stomach and a distal end of the tubular member being positioned in an intestine of the patient.

One exemplary embodiment of a tubular member 142 and application thereof to the patient is illustrated in FIGS. 12 and 13. The tubular member 142 can be cannulated and, as in the illustrated embodiment, can have an inner lumen (not shown) extending therethrough between proximal and distal terminal ends 142p, 142d thereof. The tubular member 142 in the illustrated embodiment of FIGS. 12 and 13 is configured as an open tube having two open terminal ends, similar to a drinking straw. However, a tubular member implanted within a patient can be configured as a closed tube or a closed loop having multiple paths. Various non-limiting embodiments of a closed tube or a closed loop having multiple paths can be found in previously mentioned PCT App. No. PCT/EP2010/060275 filed Jul. 16, 2010 and entitled "A Device And Method For Directing Bile From The Gallbladder In the Intestine."

The tubular member 142 can be applied to the patient in any way, as will be appreciated by a person skilled in the art. As in the illustrated embodiment, the proximal terminal end 142p of the tubular member 142 can be advanced through the patient's mouth, through the esophagus 102, into the stomach 104, and to a position adjacent the incision 122. As shown in FIG. 12, with the proximal terminal end 142p positioned adjacent the incision 122, an intermediate portion 142i of the tubular member 142 can extend through the esophagus 102 such that the distal terminal end 142d is positioned in the esophagus 102, the mouth, or outside the patient's body when the proximal terminal end 142p is secured to the gall bladder 110.

The proximal terminal end 142p can be secured to the gall bladder 110 in any way, such as by attaching the proximal terminal end 14-2p to the stomach and gall bladder walls 104w, 110w at the incision 122 formed therein using one or more anchors, e.g., by applying at least one staple and a supplemental adhesive. Relative sizes of the incision 122 and the tubular member 142 can be such that a seal is formed between the gall bladder 110 and the stomach 104 such that bile exiting the gall bladder 110 for eventual, possible entrance into the intestine 106 can only do so by passing into the proximal terminal end 142p of the tubular member 142. In other words, a seal can be formed between at least the tubular member 142 and the gall bladder wall 110w such that bile cannot leak out of the gall bladder 110 through the incision 122 to move into the stomach 104 where it could contact an inner wall of the stomach 104. Formation of a seal between the gall bladder 110 and the stomach 104 can be formed and/or enhanced by application of a biocompatible sealant (not shown), such as an adhesive between the tubular member 142 and the gall bladder wall 110w around a perimeter of the incision 122.

Figure 14:
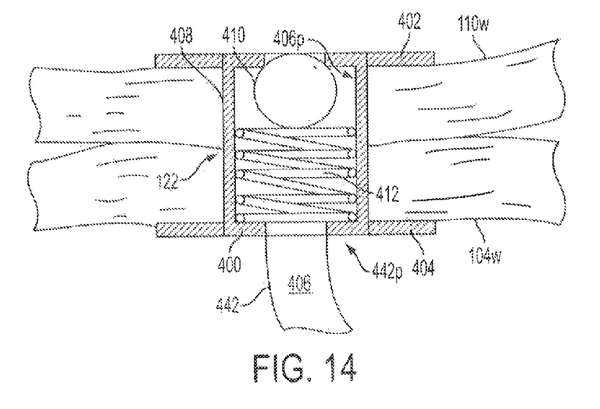
FIG. 14 is a cross-sectional view of one embodiment of a unidirectional valve at a proximal end of a tubular member.

FIG. 14 illustrates another exemplary embodiment of a tubular member 442 having a unidirectional valve 400 at a proximal terminal end 442p thereof. Various non-limiting embodiments of unidirectional valves can be found in previously mentioned PCT App. No. PCT/EP2010/060275 filed Jul. 16, 2010 and entitled "A Device And Method For Directing Bile From The Gallbladder In the Intestine." Although the illustrated unidirectional valve 400 includes a one-way check valve, as mentioned above, the tubular member 442 can include any type of unidirectional valve. The tubular member 442 can include a first portion 402 configured to be attached to a first tissue wall, e.g., the gall bladder wall 110w, and a second portion 404 configured to be attached to a second tissue wall, e.g., the stomach wall 104w. The first and second portions 402, 404 can include the unidirectional valve 400 positioned therebetween and can define a proximal portion 406p of an inner lumen 406 of the tubular member 442 such that the unidirectional valve 400 can be arranged in a flow path of the inner lumen 406. The unidirectional valve 400 can include a valve housing 408 and a shutter 410, e.g., a ball shutter, biased by a spring 412 in a closed position in which the flow path of the inner lumen 406 is shut, e.g., such that fluid cannot flow into or out of the inner lumen 406 through the tubular member's proximal terminal end 442p. The shutter 410 can be displaceable by a predetermined bile pressure on the gall bladder side of the valve 400 to an opening position in which the flow section is at least partially free to allow a flow through the valve 400. A possible pressure increase on the stomach side of valve 400 would push the shutter 410 even more in its closed position, preventing a backflow, e.g., a backflow of chime from the intestine, towards the gall bladder 110 or the biliary tract. The valve housing 408, the shutter 410, and the spring 412 can be formed from a biocompatible material, such as titanium, stainless steel or a polymer, e.g., Poly(methyl methacrylate).

Figure 15:
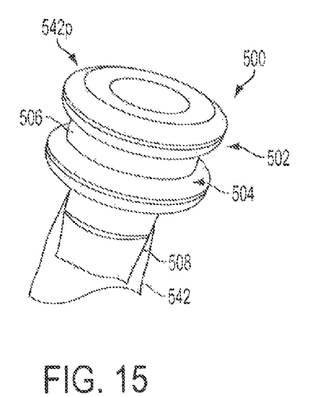
FIG. 15 is a perspective, partially transparent view of another embodiment of a unidirectional valve at a proximal end of a tubular member.
Figure 16:
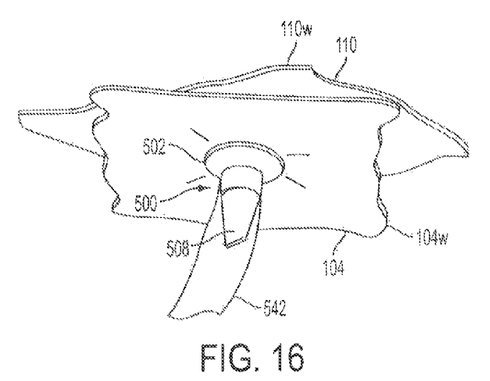
FIG. 16 is a perspective, partially transparent view of the unidirectional valve of FIG. 15 applied to stomach and gall bladder walls.

FIGS. 15 and 16 illustrate another exemplary embodiment of a tubular member 542 having a unidirectional valve 500 at a proximal terminal end 542p thereof. The unidirectional valve 542 can include a tubular body 502 having an external surface 504. The external surface 504 can form a peripheral annular cavity 506 configured to receive a rim of the tubular member 542 to connect the unidirectional valve 500 thereto. The tubular body 502 can be elastically deformable to allow radial deformation thereof during insertion into the stomach and gall bladder walls 104w, 110w and subsequent elastic radial expansion to accomplish a shape fit or interference fit between the unidirectional valve 500 of the tubular member 542 and the stomach and gall bladder walls 104w, 110w. In an exemplary embodiment, the unidirectional valve 500 can include a duckbill valve shutter 508.

Figure 17:
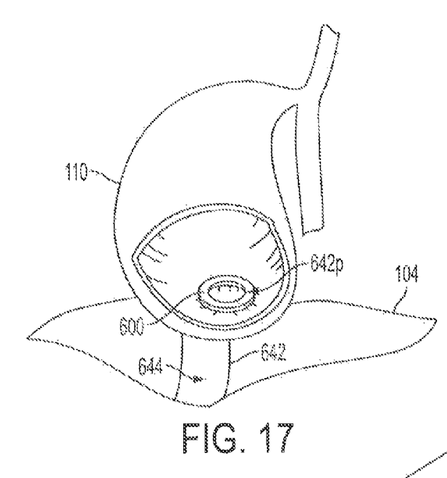
FIG. 17 is a perspective, partial cutaway view of another embodiment of a unidirectional valve at a proximal end of a tubular member applied to stomach and gall bladder walls.
Figure 18:
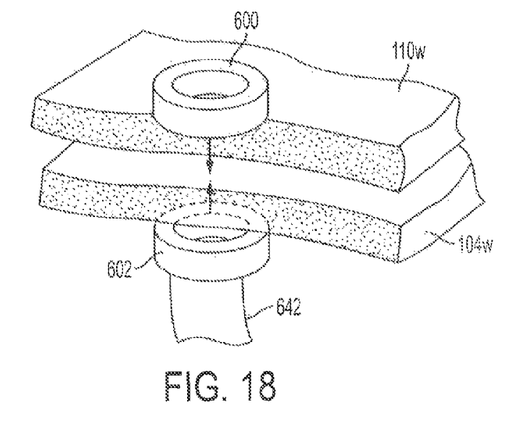
FIG. 18 is a perspective view of the unidirectional valve of FIG. 17 being applied to the stomach and gall bladder walls.
Figure 19:
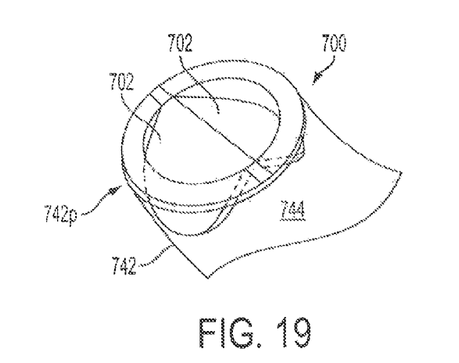
FIG. 19 is a perspective, partially transparent view of another embodiment of a unidirectional valve at a proximal end of a tubular member.

FIGS. 17 and 18 illustrate another exemplary embodiment of a tubular member 642 including first and second pressure rings 600, 602 configured to connect to each other in a clamping relationship, e.g., by snap fit, press fit, magnetic attraction, screw connection, etc., and configured to secure the stomach and bladder walls 104w, 110w in anastomosis and secure a proximal terminal end 642p of the tubular member 642 thereto. Although not shown, the tubular member 642 can include a unidirectional valve, e.g., a duckbill valve coupled to the second pressure ring 602 and positioned within an inner lumen 644 of the tubular member 642, or a double-sided flapper valve. FIG. 19 illustrates an exemplary embodiment of a double-sided flapper valve 700 positioned at a proximal terminal end 742p of a tubular member 742. Generally, flaps 702 of the flapper valve 700 can be configured to be displaceable by a predetermined bile pressure on the gall bladder side of the valve 700 to an open configuration in which fluid is at least partially free flow from the gall bladder 110 and through the valve 700 to advance into an inner lumen 744 of the tubular member 742. A possible pressure increase on an opposite side of the valve 700, e.g., on the stomach side, would push the flaps 702 even more in a closed position, thereby preventing a backflow toward the gall bladder 110 or biliary tree. Various non-limiting embodiments of flapper valves can be found in previously mentioned PCT App. No.

PCT/EP2010/060275 filed Jul. 16, 2010 and entitled "A Device And Method For Directing Bile From The Gallbladder In the Intestine."

With the proximal end of the tubular member positioned in the gall bladder 110, e.g., using the unidirectional valve 400 of FIG. 14, using the pressure rings 600, 602 of FIGS. 17 and 18, etc., the intermediate portion of the tubular member can be positioned through the stomach 104, and the distal end of the tubular member can be positioned in the intestine 106. However, as mentioned above, the tubular member can be positioned in the gall bladder 110, the stomach 104, and the intestine 106 in any order, e.g., first positioning the tubular member's distal end in the intestine 106, etc. In one exemplary embodiment, when the proximal terminal end 142p of the tubular member 142 has been secured to the gall bladder 110, as illustrated in FIG. 13, the intermediate portion 142i of the tubular member 142 can next be positioned in the stomach 104, and then the distal terminal end 142d of the tubular member 142 can be positioned in the intestine 106. One or more surgical tools can be advanced into the stomach 104, e.g., a grasper (not shown) advanced through a working channel of the gastroscope 120, to help position the tubular member's intermediate portion 142i and distal terminal end 142d, e.g., by grasping and manipulating the tubular member 142 using opposed jaws of the grasper.

As mentioned above, any length of the tubular member's intermediate portion 142i can be positioned through the stomach 104. The tubular member's intermediate portion 142i can be secured to the stomach wall 104, e.g., using at least one anchor, or, as in the illustrated embodiment of FIG. 13, the tubular member's intermediate portion 142i can be loose or untethered within the stomach cavity.

As also mentioned above, the tubular member's distal terminal end 142d can be positioned at any location in the intestine 106. The tubular member's distal terminal end 142d can be secured to a wall of the intestine 106, e.g., using at least one anchor. Alternatively, as shown in the embodiment illustrated in FIG. 13, the tubular member's distal terminal end 142d can be loose within the intestine 106, with a natural distal-direction flow in the intestine 106 providing adequate force to retain the tubular member's distal terminal end 142d therein. A total longitudinal length of the tubular member 142 between its proximal and distal terminal ends 142p, 142d can define how far the tubular member's distal terminal end 142d can distally advance through the intestine 106. When the tubular member's distal terminal end 142d is initially positioned in the intestine 106, it can be positioned proximal to a desired position of the tubular member's distal terminal end 142d in the intestine 106, e.g., proximal to the ampulla of Vater 134. Gravity and the natural distal-direction flow in the intestine 106 distally advance the tubular member's distal terminal end 142d through the intestine 106 over time such that the tubular member's distal terminal end 142d becomes positioned in the desired position, e.g., distal to the ampulla of Vater 134. Allowing gravity and natural intestinal flow to distally advance the tubular member's distal terminal end 142d through the intestine 106, rather than surgically pushing the tubular member's distal terminal end 142d therethrough, can help prevent damage to the intestine 106 and/or to the tubular member's distal terminal end 142d.

The tubular member can optionally include a weight 144 in a distal portion thereof, e.g., adjacent the tubular member's distal terminal end 142d. The weight 144 can be configured to help retain the tubular member's distal terminal end 142d in the intestine 106 and/or to help the tubular member's distal terminal end 142d naturally advance distally through the intestine 106 without the tubular member's distal terminal end 142d having to be artificially advanced or artificially pushed down the intestine 106. The weight 144 can have a variety of sizes, shapes, and configurations. In one embodiment, the weight 144 can include a ring formed from a biocompatible metallic material, such as stainless steel or titanium, disposed around a perimeter of the tubular member 142 in a distal portion thereof. Such a weight 144 can, for non-limiting example, be wrapped around an outer surface of a tubular member formed from a different, lighter material and/or be wrapped around an inner surface of a tubular member formed from a different, lighter material.

When the tubular member 142 has been implanted within the patient with the proximal and distal terminal ends 142p, 142d thereof positioned as desired, the gastroscope 120 and any other surgical tools advanced into the patient, e.g., a grasper, can be removed from the patient. The tubular member 142 can thereby be left implanted within the patient to divert bile from the gall bladder 110 to the intestine 106. In an exemplary embodiment, the tubular member 142 can be removed from the patient in a subsequent surgical procedure.

A patient having a tubular member implanted therein can concurrently receive one or more additional treatments. For non-limiting example, the patient can be treated with at least one medication, such as an antibiotics and an chronic proton pump inhibitor (PPI), which can help address any potential of gall bladder and retrograde hepatobiliary contamination by gastric juices.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a tubular member, an anchor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising: positioning a first terminal end of a tubular member in a gall bladder of a patient; positioning an intermediate portion of the tubular member through a stomach of the patient; positioning a second terminal end of the tubular member in an intestine of the patient to allow bile in the gall bladder to flow into an inner lumen of the tubular member through the first terminal end of the tubular member, flow through the inner lumen in the intermediate portion of the tubular member through the stomach, and flow out of the inner lumen at the second terminal end of the tubular member and into the intestine; and obstructing a common bile duct of the patient such that bile in the gall bladder cannot flow through the common bile duct to the intestine, and such that pancreatic fluid can flow from a pancreas of the patient to the intestine.

2. The method of claim 1, further comprising forming a seal between the gall bladder and the stomach such that bile from the gall bladder cannot flow into the stomach to contact an inner wall of the stomach.

3. The method of claim 1, further comprising securing a wall of the gall bladder to a wall of the stomach.

4. The method of claim 3, further comprising incising the wall of the gall bladder and the wall of the stomach proximate to the securement of the wall of the gall bladder to the wall of the stomach, wherein the tubular member passes from the gall bladder to the stomach through the incisions formed in the wall of the gall bladder to the wall of the stomach.

5. The method of claim 3, wherein securing a wall of the gall bladder to a wall of the stomach comprises applying at least one anchor to the wall of the gall bladder and to the wall of the stomach.

6. The method of claim 5, wherein the at least one anchor is bioabsorbable.

7. The method of claim 1, wherein positioning the first terminal end of the tubular member comprises attaching the tubular member to a wall of the gall bladder with at least one anchor.

8. The method of claim 1, wherein positioning the second terminal end of the tubular member comprises applying a weight to the tubular member configured to maintain the second terminal end of the tubular member in the intestine.

9. The method of claim 1, wherein positioning the second terminal end of the tubular member comprises positioning the second terminal end at a jejunum of the intestine.

10. The method of claim 1, wherein positioning the first terminal end of the tubular member, positioning the intermediate portion of the tubular member, and positioning the second terminal end of the tubular member is performed using an instrument inserted through a natural orifice of the patient.

11. A surgical method, comprising: advancing an endoscope into a stomach of a patient to visualize a gall bladder of the patient through a wall of the stomach; attaching a wall of the gall bladder to the wall of the stomach; positioning a proximal end of a tubular member in the gall bladder; positioning an intermediate portion of the tubular member through the stomach; positioning a distal end of the tubular member in an intestine of the patient such that bile can flow in the tubular member from the gall bladder, through the intermediate portion of the tubular member, and to the intestine; and obstructing a common bile duct of the patient such that bile in the gall bladder cannot flow through the common bile duct to the intestine, and such that pancreatic fluid can flow from a pancreas of the patient to the intestine.

12. The method of claim 11, wherein advancing an endoscope into a stomach of a patient comprises advancing the endoscope through a mouth and an esophagus of the patient.

13. The method of claim 11, further comprising removing the endoscope from the patient and leaving the tubular member implanted in the patient with the proximal end of the tubular member positioned in the gall bladder, the intermediate portion of the tubular member positioned in the stomach, and the distal end of the tubular member positioned in the intestine.

14. The method of claim 11, wherein the tubular member forms a barrier between bile flowing therethrough and the stomach such that bile cannot come into direct contact with an inner wall of the stomach.

15. The method of claim 1, further comprising inserting a plug in a common bile duct of a patient distal to a pancreatic duct.

16. A surgical method, comprising: attaching a wall of a gall bladder to a wall of a stomach; after attaching the wall of the gall bladder to the wall of the stomach, forming an incision through the wall of the gall bladder and an incision through the wall of the stomach such that the incisions are substantially aligned; positioning a proximal end of a tubular member in the gall bladder; positioning an intermediate portion of the tubular member through the stomach such that the tubular member extends through the incisions between the gall bladder and the stomach; positioning a distal end of the tubular member in an intestine of the patient such that bile can flow in the tubular member from the gall bladder, through the intermediate portion of the tubular member, and to the intestine; and inserting a plug into a common bile duct of the patient proximal to an intersection point where the pancreatic duct meets the common bile duct such that bile in the gall bladder cannot flow through the common bile duct to the intestine and pancreatic fluid can flow from a pancreas to the intestine.

17. The method of claim 16, wherein attaching the wall of the gall bladder to the wall of the stomach comprises applying at least one anchor to the wall of the gall bladder and to the wall of the stomach.

* * * * *